United States Patent
Barda

(10) Patent No.: US 6,878,310 B2
(45) Date of Patent: Apr. 12, 2005

(54) CARBOXYLATE-CONTAINING ALKYLTIN HEAT STABILIZER

(75) Inventor: Henry J. Barda, North Brunswick, NJ (US)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 10/432,112
(22) PCT Filed: Nov. 27, 2001
(86) PCT No.: PCT/US01/44362
§ 371 (c)(1),
(2), (4) Date: May 19, 2003
(87) PCT Pub. No.: WO02/42370
PCT Pub. Date: May 30, 2002

(65) Prior Publication Data
US 2004/0011998 A1 Jan. 22, 2004

Related U.S. Application Data
(60) Provisional application No. 60/253,657, filed on Nov. 27, 2000.

(51) Int. Cl.$^7$ .................. C09K 15/10; C09K 15/32; C08K 5/58; C08K 5/57; C08L 27/06
(52) U.S. Cl. ............. 252/406; 252/182.15; 252/182.17; 252/182.3; 252/182.33; 524/180; 524/181; 524/144; 524/567
(58) Field of Search .................. 252/182.15, 182.33, 252/406, 183.11, 182.17, 182.3; 524/180, 181, 144, 567

(56) References Cited

U.S. PATENT DOCUMENTS

| | | | |
|---|---|---|---|
| 3,565,930 A | | 2/1971 | Kauder et al. |
| 3,565,931 A | | 2/1971 | Brecker |
| 3,654,222 A | | 4/1972 | Stapfer et al. |
| 3,769,263 A | | 10/1973 | Mayo et al. |
| 3,817,915 A | | 6/1974 | Kauder et al. |
| 4,080,363 A | | 3/1978 | Hutton et al. |
| 4,146,518 A | * | 3/1979 | Minagawa et al. ......... 524/178 |
| 4,255,320 A | | 3/1981 | Brecker et al. |
| 4,312,769 A | * | 1/1982 | Pratt .......................... 508/505 |
| 4,552,907 A | * | 11/1985 | Sato et al. .................. 523/455 |
| 5,527,842 A | * | 6/1996 | Hoch .......................... 524/180 |

FOREIGN PATENT DOCUMENTS

| | | | | |
|---|---|---|---|---|
| EP | 1004625 | | 5/2000 | ............ C08K/5/57 |
| GB | 1297931 | | 11/1972 | ........... C08F/45/58 |

* cited by examiner

Primary Examiner—Joseph D. Anthony
(74) Attorney, Agent, or Firm—Richard P. Fennelly

(57) ABSTRACT

A stabilizer composition, suitable for use in polyvinyl chloride compositions, can be formed by reacting a mixture of monoalkyltin trichloride, such as butyltin trichloride, and dialkyltin dichloride, such as dibutyltin dichloride, with at least one carboxylic acid, such as 2-ethylhexanoic acid, and 2-mercaptoethanol, in the presence of base, followed by reaction of the resulting product with a sulfide reagent, such as sodium sulfide. The final composition comprises a complex mixture of alkyl tin carboxylates and/or mercaptides, and of monoalkyltin sulfides and dialkyltin sulfides.

13 Claims, No Drawings

CARBOXYLATE-CONTAINING ALKYLTIN HEAT STABILIZER

This application is a 371 of PCT/US01/44362 filed Nov. 27, 2001 which claims benefit of provisional application 60/253,657 filed Nov. 27, 2000.

Poly(vinyl chloride) degrades when subjected to stress in the form of mechanical shear, heat, or electromagnetic radiation. Oxygen participates in the degradative process. Poly(vinyl chloride)-based formulations need to be stabilized during compounding, manufacture, and use in order to be commercially viable products. To that end, heat stabilizers are added to poly(vinyl chloride) formulations, sometimes together with antioxidants and light stabilizers. Poly(vinyl chloride) degradation is monitored by color development over time, conventionally divided in terms of early color, intermediate color (or color hold), and long term color. Different stabilizing compounds, and mixtures thereof, are better at controlling different stages of color development, or at light stabilization, so that different mixtures are necessary for different applications.

Heat stabilizers also have to meet material handling and lubricity requirements. Contemporary heat stabilizers are preferably liquids of suitable concentration, viscosity, and shelf stability. To achieve these goals one or more diluent and/or lubricant may be added to the heat stabilizer mixture.

Organotin compounds are one class of heat stabilizer. They are tin (IV) compounds, which are mono- or disubstituted with alkyl, or 2-carboalkoxyethyl, groups. The balance of the substituents includes oxygen or sulfur ligands, typically carboxylates, mercaptides, and sulfides.

Alkyltin carboxylates were the first to be commercialized. They are still used where light stability is important, but have mostly been replaced by better performing mercaptides, and mixtures of mercaptides and sulfides. Examples of these carboxylate-free stabilizers, which are used below in the Examples as controls, are:

Interstab T-5003, a mixed butyltin mercaptide/sulfide containing 26% tin, available from Akzo Nobel.

Interstab T-7020, a mixed methyltin mercaptide containing 19% tin, available from Akzo Nobel.

Advastab TM-697, a mixed methyltin mercaptide/sulfide in diluent(s), containing 10.5% tin, available from Rohm & Haas.

Surprisingly, it has been found, in a preferred embodiment of this invention, that mixed buytltin carboxylates/sulfides, containing a small amount of mercaptide, derived from 2-mercapoethanol, perform comparably to the aforementioned carboxylate-free stabilizers. Thus, it can be viewed that one preferred embodiment of the present invention relates to a liquid heat stabilizer, of suitable viscosity and shelf stability, which results from the reaction of a portion of a mixture of monoalkyltin trichloride ($RSnCl_3$, with R being alkyl of from 1 to about 12 carbon atoms) and dialkyltin dichloride ($R_2SnCl_2$, with R being alkyl of from 1 to about 12 carbon atoms) with a carboxylic acid, or mixture of such acids, and 2-mercaptoethanol, in the presence of a suitable base, followed by reaction of the remaining, unreacted portion of tin chlorides with a suitable sulfide reagent.

The first reaction step involving reaction of the mixture of alkyl group-containing tin chlorides involves use of a lower gram equivalent amount of selected carboxylic acid, 2-mercaptoethanol, and base to insure that only a portion of the original tin chloride reagent mixture is reacted, leaving the remaining portion for reaction with the sulfide reagent. The reactions of each of these tin chloride reagents can be generally depicted as follows (with LH being the source of the ligand "L", with LH, in the case of the acid being R'C(O)OH, with R' being alkenyl of from about twelve to about twenty carbon atoms in length or alkyl of from about eight to about twelve carbon atoms in length and, in the case of 2-mercaptoethanol, being $HOCH_2CH_2SH$):

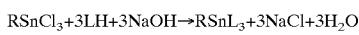

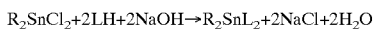

Thus, a mixture of alkyl tin tricarboxylates and trimercaptides and of dialkyltin dicarboxylates and dicarboxylates will be formed with a remaining portion of the original tin chloride reagent mixture remaining for reaction with a suitable sulfide reagent (e.g., an alkali metal sulfide such as sodium sulfide) to give a mixture of monoalkyltin sulfides and dialkyltin sulfides. This reaction can be illustrated as follows:

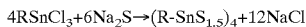

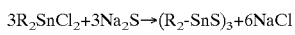

The final stabilizer composition therefore is a complex mixture of alkyl tin carboxylates, mercaptides, and of carboxylate(s)/mercaptide(s) compounds (referred to below as "alkyltin carboxylate(s)/mercaptide(s)" and of monoalkyltin sulfides and dialkyltin sulfides. The complexity of the first mentioned component is due to the propensity of the carboxylate and mercaptide moieties to react in a rather indiscriminating mnanner with the starting mixture of organotin chlorides. The types of products that can comprise the "alkyltin carboxylate(s)/mercaptide(s)" component of the final composition are the following (with "A" indicating carboxylate and "M" indicating mercaptide: RSnAAA; RSnAAM; RSnAMM; RSnMMM; RRSnAA; RRSnAM; and RRSnMM. The "alkyltin carboxylate(s)/mercaptide(s)", monoalkyltin sulfide, and dialkyltin sulfide components are present in the following general amounts (weight % of the total formulation:

| Component | Weight %* |
| --- | --- |
| Alkyltin carboxylate(s)/mercaptide(s) | 4 to 94 |
| Monoalkyltin sulfide | 3 to 48 |
| Dialkyltin sulfide | 3 to 48 |

*Provided that the three components add to 100 weight %.

The following provides a description of the respective percentages (on an equivalent basis) of the various reagents that can be used herein to form the ultimate stabilizer composition:

| Compound | Equivalent %* |
|---|---|
| Alkyltin trichloride | 10 to 90 |
| Dialkyltin dichloride | 10 to 90 |
| Carboxylic acid | 30 to 70 |
| 2-Mercaptoethanol | 8 to 20 |
| Sulfide | 8 to 60 |

*Provided that the two tin chlorides add to 100 equivalent %, and the three ligand sources add to 100 equivalent %.

The Examples that follow illustrate certain of the preferred embodiments of the present invention.

EXAMPLES

To a one or two liter reaction flask was added water (255.2 g), a mixture of 60 weight percent butyltin trichloride and 40 weight percent dibutyltin chloride (232.6 g), carboxylic acid, and 2-mercaptoethanol, if any, as described in Tables I–III, below. With stirring, a 50 weight percent solution of sodium hydroxide, equivalent to the combined carboxylic acid and 2-mercaptoethanol, was added dropwise at 50–80° C. After stirring for fifteen minutes at 80° C., sodium sulfide, if any, as in Tables I–III was added incrementally at 80° C. over one hour. After stirring for fifteen minutes, the content was transferred to a separatory funnel, the phases were separated, and the product was transferred back to the reaction flask. It was dehydrated under vacuum, and filtered through a layer of diatomaceous earth. The product was stored for four weeks at ambient conditions to determine whether it solidified in part or in whole. If it remained totally liquid, its viscosity and tin content were determined.

Those products that remained liquid and were of low viscosity were added to the formulation in Table IV on an equal tin basis as in Tables I–III. A 66 g charge was masticated for two minutes at 200° C. and 60 rpm in a Brabender Plasticorder equipped with a number 6 electrically heated mixing head. Whether the polymer formulation fused or not was noted.

The stabilization effectiveness of products from Examples 9 and 10, in Table V, was compared to the commercial stabilizer Interstab T-5003. The dynamic stability evaluation proceeded as described above, in the formulation in Table IV, and the. stabilizer level in Table V, except that samples were removed periodically. The Hunter L value of the samples was determined and reported in Table VI.

The product from Example 7, Table III, was formulated as part of Example 11, Table VII, and compared to the commercial stabilizer Advastab TM-697, in the formulation described in Table V, using the levels in Table VII, under the same conditions as above. The Hunter L value was determined and reported in Table VII.

The stabilizing effectiveness of the product from Example 3, Table I, was compared to commercial stabilizer Interstab T-7020. The dynamic stability evaluation proceeded in a Brabender Plasticorder under the following conditions: 63 g charge, 180° C., 100 rpm, three minute samples, using the formulation described in Table IX. The Hunter L value was determined and reported in Table X.

The carboxylic acids were chosen from aliphatic compounds containing from 2–30 carbon atoms, and which were saturated, monounsaturated, or polyunsaturated.

The diluents, when present, were one or more of the following: alcohols; phenols; mercaptans; ethers; ketones; carboxylic acids; carboxylic acid esters; carboxylic acid amides; hydrocarbons; etc.

Telura 323 is a naphthenic hydrocarbon, industrial process oil, available from Exxon.

Hunter L values: the higher the numbers, the better the color. Values that differed by 2 units or less, were considered to be the same, within experimental error. All amounts for the additives, unless otherwise expressed, is given in grams:

TABLE I

| Example: | 1 | 2 | 3 |
|---|---|---|---|
| Oleic acid | 583.0 | 296.2 | 198.8 |
| 2-Mercaptoethanol | — | — | 26.9 |
| Sodium sulfide (62%) | — | 60.5 | 60.5 |
| Tin, % | 12.5 | — | 23.4 |
| State after storage | liquid | solid | liquid |
| Viscosity (Stokes at 25° C.) | 0.5 | — | 1.0 |
| Stabilizer level, phr | 1.63 | — | 0.89 |
| Brabender, two minutes | unfused | — | unfused |

TABLE II

| Example: | 4 | 5 | 6 |
|---|---|---|---|
| 2-Ethylhexanoic acid | 297.6 | 156.2 | 101.5 |
| 2-Mercaptoethanol | — | — | 26.9 |
| Sodium sulfide (62%) | — | 60.5 | 60.5 |
| Tin, % | — | 28.5 | 31.4 |
| State after storage | solid | liquid | liquid |
| Viscosity, Stokes at 25° C. | — | 55 | 4 |
| Stabilizer level, phr | — | — | 0.78 |
| Brabender, 2 minutes | — | — | fused |

TABLE III

| Example: | 7 | 8 |
|---|---|---|
| 2-Ethylhexanoic acid | 96.5 | 91.5 |
| 2-Mercaptoethanol | 29.6 | 32.5 |
| Sodium sulfide (62%) | 60.5 | 60.5 |
| Tin, % | 31.6 | — |
| State after storage, | liquid | solid |
| Viscosity (Stokes at 25° C.) | 5 | — |
| Stabilizer level, phr | 0.78 | — |
| Brabender, 2 minutes | fused | — |

TABLE IV

| Poly(vinyl chloride), 225, OxyChem | 100.0 |
|---|---|
| Impact modifier, Paraloid KM334, Rohm & Haas | 5.0 |
| Processing aid, Paraloid K12ON, Rohm & Haas | 0.5 |
| Calcium stearate, Norac | 1.1 |
| External lubricant, Rheolube 3155, Allied Chemical | 1.2 |
| Calcium carbonate, Omyacarb UFT, Omya | 12.0 |
| Titanium dioxide, R-960, Dupont | 2.0 |

TABLE V

| Example: | 9 | 10 | T-5003 |
|---|---|---|---|
| Product Example 7, wt. % | 82.4 | — | — |
| Product Example 6. wt. % | — | 82.8 | — |
| Soybean oil, wt. % | 17.6 | 17.2 | |

TABLE V-continued

| Example: | 9 | 10 | T-5003 |
|---|---|---|---|
| Tin, % | 26.0 | 26.0 | 26.0 |
| Stabilizer level, phr | 0.8 | 0.8 | 0.8 |

TABLE VI

Hunter L values

| | Minutes: | | | | | | | | | |
|---|---|---|---|---|---|---|---|---|---|---|
| | 2 | 4 | 6 | 8 | 10 | 12 | 14 | 16 | 18 | 20 |
| Example 9: | 90.5 | 86.6 | 83.4 | 82.5 | 80.2 | 77.6 | 74.2 | 74.6 | 67.4 | 65.9 |
| Example 10: | 89.9 | 89.8 | 84.1 | 84.8 | 82.5 | 80.1 | 77.8 | 74.9 | 68.4 | 68.8 |
| T-5003: | 90.7 | 85.9 | 83.8 | 82.2 | 79.4 | 78.2 | 74.6 | 72.4 | 69.6 | 66.3 |

TABLE VII

| Example: | 11 | TM-697 |
|---|---|---|
| Product Example 7, wt. % | 33.2 | — |
| 2-Mercaptoethyl tallate, wt. % | 15.0 | — |
| Telura 323, wt % | 51.3 | — |
| 2-Mercaptoethanol, wt % | 0.5 | — |
| Tin, % | 10.5 | 10.5 |
| Stabilizer level, phr | 1.06 | 1.06 |

TABLE VIII

Hunter L Values

| | Minutes: | | | | | |
|---|---|---|---|---|---|---|
| | 3 | 6 | 9 | 12 | 15 | 18 |
| Example 11 | 89.3 | 88.5 | 86.1 | 80.2 | 74.6 | 70.9 |
| TM-697 | 84.0 | 77.6 | 70.8 | 78.5 | 72.5 | 66.9 |

TABLE IX

| Poly(vinyl chloride), 1066, Georgia Gulf | 100.0 |
|---|---|
| Processing aid, K-120N, Rohm & Haas | 1.5 |
| Impact modifier, KM-318, Rohm & Haas | 6.0 |
| Titanium dioxide, R-101, Dupont | 2.0 |
| Calcium carbonate, Omyacarb UFT, Omya | 3.0 |
| Lubricant, MIP-1880, Rheochem | 2.4 |
| Lubricant, RL-710, Rheochem | 0.5 |
| Stabilizer | 1.5 |

TABLE X

Hunter L values

| | Minutes: | | | | | | | | | |
|---|---|---|---|---|---|---|---|---|---|---|
| | 3 | 6 | 9 | 12 | 15 | 18 | 21 | 24 | 27 | 30 |
| Example 3 | 90.6 | 88.9 | 86.9 | 84.2 | 81.6 | 78.4 | 75.2 | 71.9 | 67.1 | 8.8 |
| T-7020 | 88.3 | 84.9 | 82.3 | 80.1 | 77.7 | 77.3 | 79.8 | 70.9 | 58.6 | 54.8 |

The previous Examples should not be construed in a limiting fashion since they are presented to merely describe certain embodiments of the present invention. The scope of protection sought is set forth in the claims that follow.

I claim:

1. A composition of matter, which is useful as a heat stabilizer for polyvinyl chloride compositions, which is obtained by reacting a portion of a mixture of monoalkyltin trichloride and dialkyltin dichloride with at lease one carboxylic acid and 2-mercaptoethanol, in the presence of base, followed by reaction of the remaining portion with a sulfide reagent.

2. A composition as claimed in claim 1 wherein the alkyl moieties are all butyl.

3. A composition as claimed in claim 1 wherein the carboxylate moieties are all 2-ethylhexanoate.

4. A composition as claimed in claim 1 wherein the alkyl moieties are all butyl and the carboxylate moieties are all 2-ethylhexanoate.

5. A composition as claimed in claim 1 wherein the carboxylate moieties are all oleate.

6. A composition as claimed in claim 1 wherein the alkyl moieties are all butyl and the carboxylate moieties are all oleate.

7. A process for forming a stabilizer composition, suitable for use in polyvinyl chloride compositions, which comprises reacting a portion of a mixture of monoalkyltin trichloride and dialkyltin dichloride with at least one carboxylic acid and 2-mercaptoethanol, in the presence of base, followed by reaction of the remaining portion with a sulfide reagent.

8. A process as claimed in claim 7 wherein the monoalkyltin trichloride is of the formula $RSnCl_3$ with R being butyl.

9. A process as claimed in claim 7 wherein the dialkyltin dichloride is of the formula $R_2SnCl_2$ with R being butyl.

10. A process as claimed in claim 7 wherein the sulfide reagent is sodium sulfide.

11. A process as claimed in claim 7 wherein the carboxylic acid is of the formula $RCO_2H$ with R being alkenyl of from about twelve to about twenty carbon atoms in length or alkyl of from about eight to about twelve carbon atoms in length.

12. A process as claimed in claim 11 wherein the carboxylic acid is 2-ethylhexanoic acid.

13. A process as claimed in claim 7 wherein the monoalkyl trichloride is butyltin trichloride, the dialkyltin dichloride is dibutyltin dichloride, the carboxylic acid is 2-ethylhexanoic acid, and the sulfide reagent is sodium sulfide.

* * * * *